United States Patent [19]

Sideris

[11] Patent Number: 5,792,179
[45] Date of Patent: Aug. 11, 1998

[54] RETRIEVABLE CARDIAC BALLOON PLACEMENT

[76] Inventor: Eleftherios B. Sideris, 1600 Coulter, Suite 200B, Amarillo, Tex. 79106

[21] Appl. No.: 864,164

[22] Filed: May 28, 1997

Related U.S. Application Data

[60] Provisional application No. 60/021,832 Jul. 16, 1996.
[51] Int. Cl.$^6$ .................................................. A61B 17/00
[52] U.S. Cl. ........................ 606/213; 606/215; 606/157; 623/2; 623/11
[58] Field of Search .......................... 606/213, 216, 606/232, 157; 128/887; 623/1, 2, 11

[56] References Cited

U.S. PATENT DOCUMENTS

| | | | |
|---|---|---|---|
| 3,671,979 | 6/1972 | Moulopoulos | 3/1 |
| 4,056,854 | 11/1977 | Boretos et al. | 3/1.5 |
| 4,836,204 | 6/1989 | Landymore et al. | 606/215 |
| 4,917,089 | 4/1990 | Sideris | 606/215 |
| 5,284,488 | 2/1994 | Sideris | 606/213 |
| 5,433,727 | 7/1995 | Sideris | 606/213 |
| 5,634,936 | 6/1997 | Linden et al. | 606/213 |

Primary Examiner—Michael Powell Buiz
Assistant Examiner—David O. Reip
Attorney, Agent, or Firm—Wendell Coffee

[57] ABSTRACT

This is an intravascular prothesis deliverable percutaneously with several cardiac applications including but not limited to heart valves, intravascular narrowings and cardiac defect occlusion. The device has a detachable sac connected through a thread or wire outside the body where it is immobilized. The device can remain inside the heart for as long as it is clinically useful in non permanent applications (valve, throttle); at any point it can be retrieved by pulling it outside the body by the holding wire/thread. In permanent applications (defect occlusion) the wire/thread can be withdrawn allowing the sac to endothelialize.

22 Claims, 3 Drawing Sheets

RETRIEVABLE CARDIAC BALLOON PLACEMENT

CROSS REFERENCE TO RELATED APPLICATION

Provisional Patent Application

Applicant filed a Provisional Application on this subject matter on Jul. 16, 1996, #60/021,832. Specific reference is made to that document.

BACKGROUND OF THE INVENTION (1) Field of the Invention

The present invention relates to intravascular prosthesis delivered percutaneously pertaining to the heart. Ordinary physicians or cardiologists have ordinary skill in the art.

(2) Description of the Related Art & Suggestion of Solution

Several patents and publications describe the use of detachable fluid filled sacs for the occlusion of arteriovenous fistulas and other small communication. In this application, the terms balloon and sac are used interchangeably. There are even publications describing attempts of occlusion of patent ductus arteriosus by detachable balloons; however, the concept of making detachable fluid filled sacs or similar devices tethered by a holding wire immobilized on the skin and therefore making them retrievable is new.

Attempts of making percutaneously introduced cardiac valves are known but they have not been popularized so far. Attempts usually try to imitate the design of either artificial mechanic valves or the biological valves. The introduction of a cage and a ball would be an imitation of the Star-Edwards valve as would the introduction of a biological valve mounted on a stint. All valves described herein are considered to be heart valves, although they might not be within the heart.

The concept of the current invention is quite original since as a ball we use a detachable fluid filled sac which does not require a cage. The sac is connected to a holding wire immobilized on the skin. It uses the natural valve annulus as a case and can be retrieved at anytime.

In the case of the pulmonic valve, the sac is placed in the main pulmonary artery. In systole the balloon can only be moved the length allowed by the holding wire; in diastole though, the sac returns to the valve annulus where it prevents any insufficiency.

In the case of tricuspid insufficiency, the sac is placed in the body of the right ventricle where in diastole it moves as limited by the holding wire; in systole though, it occludes the insufficient tricuspid valve.

In the case of mitral valve insufficiency, the sac is positioned transeptally in the left ventricle occluding the mitral valve in systole and allowing left ventricular filling in diastole.

In the case of aortic insufficiency, the balloon is placed transeptally, or left after ventricular needle puncture. An optional stabilizing wire sutured at a predetermined distance on the holding wire can secure further the position of the fluid filled sac on a proximal structure (atrial septum for mitral valve and aortic valve, inferior vena cava for tricuspid valve, pulmonary artery for pulmonic valve).

Since cardiac operations for valve replacement are dangerous and costly, and since there is not a perfect artificial valve so far, a percutaneously introduced and retrieved valve makes good sense, even if it has to be replaced more frequently.

Pulmonary artery banding is a surgical operation for the restriction of excessive pulmonary flow and pressure in cases of large ventricular septal defects or more complex cases where primary repair is not possible. This process of reducing flow of fluids will be referred to as "throttling" or "restricting" or even "banding", even when bands are not used. This surgical operation is not only associated with morbidity, but there is significant risk in the re-operation to take down the band as well a risk of pulmonary artery deformity requiring surgical angioplasty. By this invention, the sac is released in the main pulmonary artery where it is immobilized not only by the holding wire but by a wire sutured on the sac and attached to the main pulmonary artery intima. It can remain in place for as long as it is effective and can be removed by simply pulling the holding wire when it is no longer needed.

Occlusion of heart defects has been achieved by the use of several double disk devices similar to the King and Mills patent (U.S. Pat. No. 3,874,388) or the Sideris patent (U.S. Pat. No. 4,917,089). All such devices require sufficient septal rim for their application; therefore, heart defects with incomplete rim, like very large ostium secundum defects, sinus venosus and ostium primum atrial septal defects, and the membranous ventricular septal defects cannot be repaired. As I have learned by sizing prior to device occlusion, a fluid filled sac requires a minimal rim to occlude a defect. If the sac, tethered by the holding wire, is allowed to be endothelialized, it can be placed to occlude the defect permanently; in such a case leaking and collapse of the sac in a few months period should not matter. The sac could be modified to be relatively flat on the septum for this application.

For the ductus arteriosus occlusion, elongated occluder sac is used on the aortic side and the ductal lumen. The sac can be secured in place with a counter-occluder in the pulmonary artery the same way as the buttoned device.

SUMMARY OF THE INVENTION (1) Progressive Contribution to the Art

The intra-cardiac devices of the current invention provide means of retrievable percutaneously delivered heart valves and occluding devices therefore avoiding the need for surgery. In the application of these fluid filled sac valves and occluders the approach is usually transvenous and invariably transcutaneous. The device is made by two basic parts comprising a detachable sac and a tethering wire connected by a connecting loop. In a preferred embodiment, the detachable sac portion of the device is made of either latex or polyurethane. A protective catheter piece, 2 mm shorter than the inflated sac, with several side-holes and a smooth end, is introduced into the sac. A special catheter is made with 0.025", 0.5–1" long needle connected to the end of the catheter. The tip of the needle is introduced inside the protective catheter piece. A piece of latex is tied over the mouth of the detachable sac and the needle. During introduction, the protective catheter piece protects the sac from the needle. After the needle catheter is pulled out, detaching the inflated sac, the latex tie seals the mouth of the sac.

In a preferred embodiment of the connecting loop, it can be made by nylon or silk in a fashion similar to the adjustable buttoned loop of the buttoned device (U.S. Pat. No. 5,284,488) for the occluding device, or as a plain round loop for the retrievable valve. The connective loop is sutured and tied securely on the mouth of the sac. The holding wire is made similar to the loading wire of the buttoned device and is attached to the connecting loop. It can remain attached to the sac as in the valve or band application, or can eventually be detached as in the occlusion application.

Summaries of the description of the devices according to application:

1. Valve application: The sac has the shape similar to a sphere. The sac is connected through a round connecting loop to the tethering wire. Dimension choice depends on prior testing with an actual sac catheter. Method of placement varies according to the valve. For the tricuspid and pulmonic valves, placement is direct transvenous through a long Mullins sheath. For the mitral and the aortic valves, the entry is transeptal. Aortic application can be also performed through direct left ventricular needle puncture. The optional stabilizing wire is positioned just above the natural pulmonic valve, in the inferior vena cava, the atrial septum and just above the aortic valve for pulmonic, tricuspid, mitral and aortic valve applications respectively.

2. Throttling application: A 0.018" Teflon coated wire with floppy ends is sutured at the level of the balloon in the center of the pulmonary artery lumen and away from the vessel wall. The device is immobilized by the holding wire.

3. Heart defect occlusion application: In this application the sac can be of different shapes (flat, sphere, or elongated) and an adjustable buttoned loop is sutured at the same end as the needle catheter entry. A counter-occluder introduced over the holding wire is buttoned with the occluder proximal to the defect chamber. As alternative to the buttoned detachable balloon already described, we can use a permanently sutured to the mouth of the balloon floppy disk which will automatically expand on the proximal chamber, holding the wire in place. If the sac remains stable the holding wire can be detached immediately, otherwise it can be secured in the groin and be withdrawn in a week.

(2) Objects of this Invention

An object of this invention is to provide devices non-surgically implanted and retrievable for the treatment of heart valve insufficiency and treatment requiring throttling fluid flow.

Another object is to provide detachable fluid filled sacs of varying size and shape for different applications.

Another object is to supply detachable sacs modified for internal throttling purposes; which are implanted without surgery, produce variable degrees of restriction according to their diameter, and can be retrieved without surgery.

Another object is to supply a detachable sac occluding devices which is superior to the double disk devices since they require minimal rim; therefore, they can be applied for defects like membranous ventricular septal defects which were nearly exclusively in the surgical domain.

Further objects are to achieve the above with devices that are sturdy, compact, durable, lightweight, simple, safe, efficient, versatile, ecologically compatible, energy conserving, and reliable, yet inexpensive and easy to manufacture, install, operate, and maintain.

Other objects are to achieve the above with a method that is rapid, versatile, ecologically compatible, energy conserving, efficient, and inexpensive.

Further objects are to achieve the above with a product that is easy to store, is safe, versatile, efficient, stable and reliable, yet is inexpensive and easy to manufacture and administer.

The specific nature of the invention, as well as other objects, uses, and advantages thereof, will clearly appear from the following description and from the accompanying drawings, the different views of which are not necessarily scale drawings.

CATALOGUE OF ELEMENTS

Figure 1A:
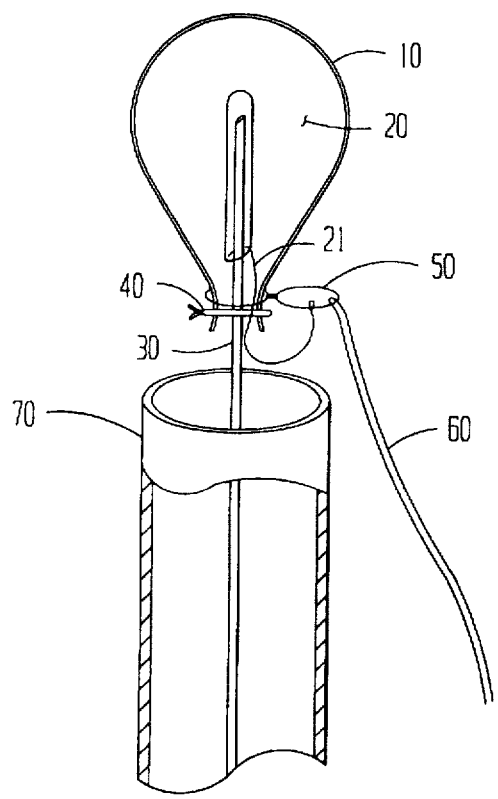
FIGS. 1a and 1b are perspective views of the preferred embodiments of the basic device during introduction and after inflation and detachment. The device is advanced by pushing the needle catheter while the sac is protected from puncture by the protective catheter piece. After sac inflation, the needle catheter is pulled out and the mouth of the sac seals by a latex valve.

As an aid to correlating the terms of the claims to the exemplary drawing(s), the following catalog of elements and steps is provided:

10 sac
20 protective catheter piece
40 latex tie (valve)
50 connecting loop
60 holding or tethering wire
70 needle catheter
80 buttoned loop
90 counter-occluder
100 nylon thread
110 stabilizing wire
111 optional stabilizing wire
120 retrieval sheath
130 floppy disk

DESCRIPTION OF THE PREFERRED EMBODIMENTS(S)

Referring to the drawings, FIG. 1 in particular, there is illustrated the basic sac device during introduction (FIG.

Figure 1B:
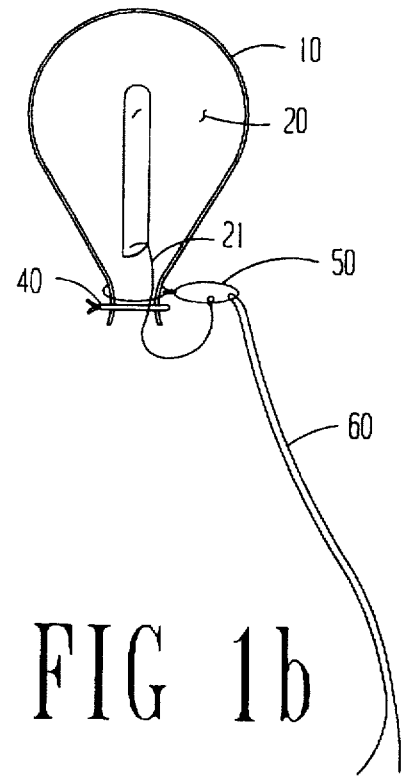
Figure 6:
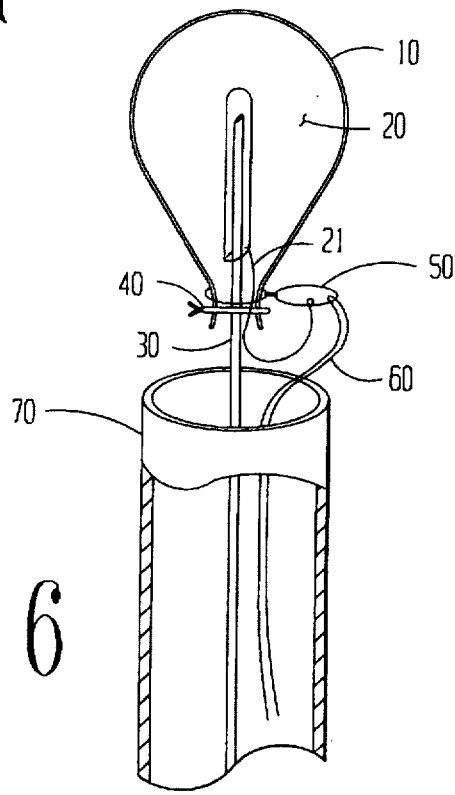

1A) and after sac inflation and detachment (FIG. 1B). In the "device during introduction" of FIG. 1A, the following components are illustrated: The sac 10, containing the protective catheter piece 20, occluded at its mouth by the latex tie acting as a valve 40. A needle catheter 70 introduces the needle 30 through the latex valve 40 inside the protective catheter piece 20. The connecting loop 50 is tied securely on the mouth of the sac 10 and is connected with the holding wire 60.

The sac 10 is made in different sizes and shapes with latex or polyurethene or other flexible materials. The protective catheter piece 20 is made by 3-5 F catheter material in a length of 2 mm shorter than the length of the non-inflated sac 10. The tip of the catheter piece is occluded so the needle 30 cannot perforate the sac 10 during introduction. There are several side holes on the catheter piece 20 to facilitate inflation and deflation.

The needle 30 is connected with the needle catheter 70. The length of the needle varies between ½" and 1" and the size is 25 GA.

The catheter part of the needle catheter 70 has an outside diameter 5 F and inside diameter 0.038"; the length of the catheter is 100 cm and a three way stopcock is connected at the end.

The connecting loop 50 is sutured and tied securely on the mouth of the sac; silk or nylon thread is used; the length of the loop is 3 mm.

The tethering wire 60 is constructed the same way as the loading wire of the buttoned device (U.S. Pat. No. 4,917,089). It is connected through the included double nylon thread with the connecting loop 50. An optional stabilizing wire 110 is sutured on the holding wire proximally to the balloon 10 at a predetermined location determined by measured distances.

FIG. 1B represents the device after sac inflation and detachment. The sac 10 is inflated with a pre-determined volume of liquid such as normal saline and contrast medium. The needle catheter 70 is pulled out of the sac 10 while the latex valve 40 occludes the mouth of the sac 10. The device is subsequently controlled by the tethering wire 60 which is connected to the sac 10 through the connecting loop 50. A stabilizing wire similar to wire 111 of FIG. 2C, if used, further secures the placement of the sac 10.

There are two mechanisms whereby the sac, acting as a valve, might allow the passage of blood. The first mechanism is by the physical movement of the sac off the sealing surface, usually the valve annulus. As the sac moves away from sealing surface as limited by the tethering wire, blood moves past the valve annulus and around the sac. A second mechanism for blood passage might be by deformation. Although not confirmed by observation, it is speculated that as the pressure builds on the side of the sac (where tethering wire is attached) the sac diameter (the diameter perpendicular to the blood flow) might tend to decrease because of the flexibility and elasticity of the sac. This deformation or decrease of diameter, if it occurs results in less restriction to blood flow.

In acting as a valve, the sac uses the physical movement mechanism, and perhaps uses the deformation mechanism, to allow flow and still be within the scope of this invention.

Figure 2A:
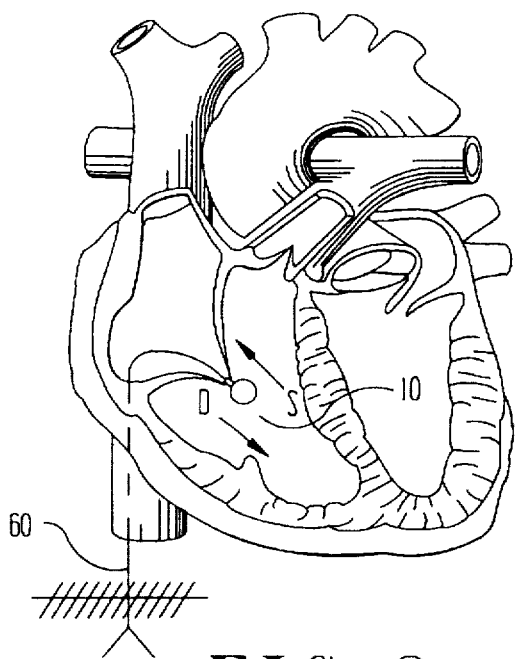
FIGS. 2a–2d are perspective views of the valve application of the device. Applications for treatment of tricuspid insufficiency (2a) and pulmonary insufficiency (2b) are described; the device is introduced directly in the right ventricle through the femoral vein. The use of a long sheath is necessary for the delivery of the device. Applications for the treatment of mitral insufficiency (2c) and aortic insufficiency (2d) are described in the appropriate drawings. The device is introduced through the femoral vein and subsequently trans-septally following standard technique. Direct transcutaneous left ventricular puncture can be also used for the aortic valve introduction.

Referring to FIG. 2A, during systole the filled sac occludes the tricuspid valve and during diastole moves forward and perhaps elongates allowing the right ventricle to fill with blood. In the tricuspid valve position the sac 10 is released in the inflow of the right ventricle held in position by holding wire 60 which is immobilized on the skin. An optional stabilizing wire 111 is positioned at the cardiac entry of the inferior vena cava.

Figure 2B:
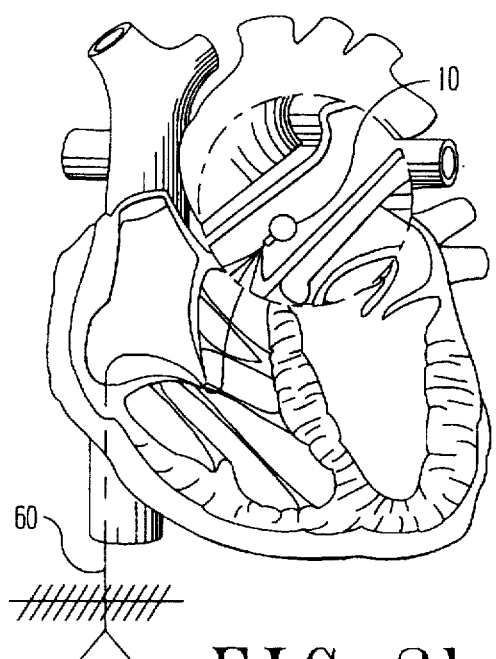
Figure 2C:
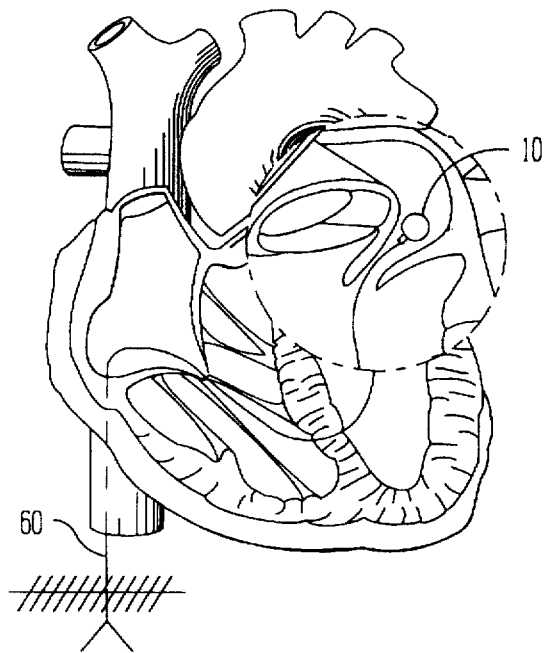
Figure 2D:
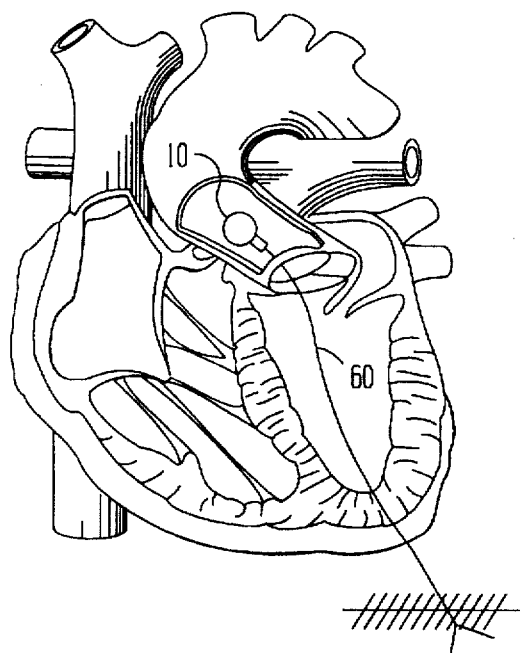

In the pulmonic valve position of FIG. 2B, the device is placed in the main pulmonary artery. The sac 10 moves forward and elongates in systole but returns occluding the valve in diastole. The optional stabilizing wire 111 is positioned just above the valve. A transeptal puncture is necessary for the mitral valve (2C) and a transeptal or apical puncture (2D) for the aortic application. The optional stabilizing wire 111 is positioned on the left side of the atrial septum.

Figure 3:
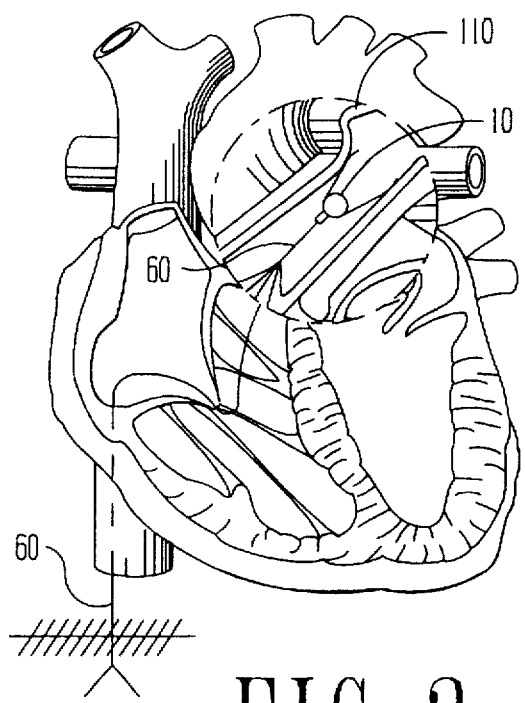
FIG. 3 is a perspective view of the internal pulmonary artery "Banding" application. A floppy wire, sutured on the device, holds the sac in the lumen of the pulmonary artery and away from the wall to avoid endothelialization and deformity. The device is introduced transvenously and is placed in the main pulmonary artery and above the pulmonic valve.
Figure 5:
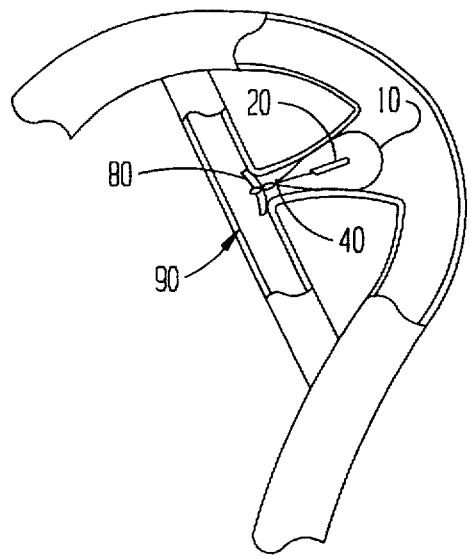

FIG. 3 shows the internal pulmonary throttling application. A floppy 0.018" Teflon coated wire (stabilizing wire) 110 is sutured at the mouth of the sac 10. The length of the wire is three times the diameter of the pulmonary artery diameter.

The stabilizing wire 110, along with the holding wire 60, keep the sac 10 in the center of the pulmonary artery and away from the wall to avoid late pulmonary artery deformity. The holding wire is immobilized on the skin and the device can be withdrawn when it is no longer needed.

Figure 4A:
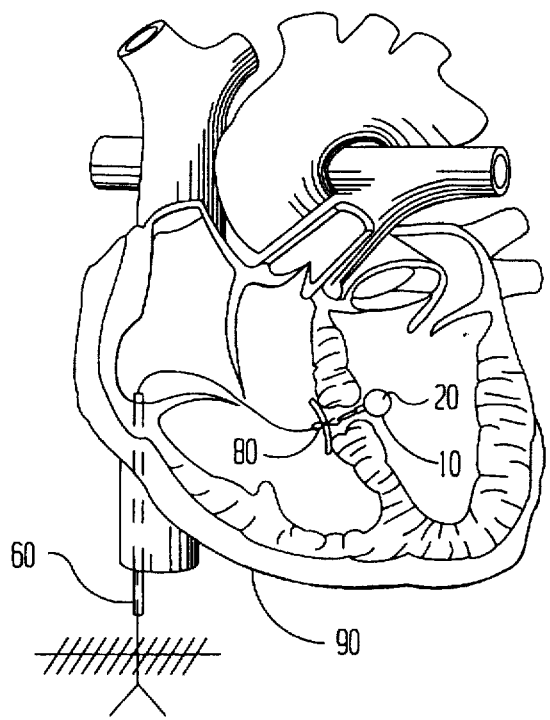
FIG. 4a is a perspective view of the heart defect occlusion application. The sac is more elongated than the basic device for the ductal application and has a buttoned loop connected at the end. A counter-occluder introduced over the holding wire is buttoned in the pulmonary artery (buttoned balloon). Release and withdrawal of the holding wire can be performed acutely or after a week.

FIG. 4A shows a heart defect occlusion application by a buttoned detachable balloon. This is a permanent implantation. The sac 10 is more elongated and a buttoned loop 80 is sutured to the mouth. A counter-occluder 90 can be buttoned over the holding wire 60 from the pulmonary artery. The sac 10 ductal occlusion should have the advantage over other methods of 100% full occlusion and independence of the result from ductal shape.

Figure 4B:
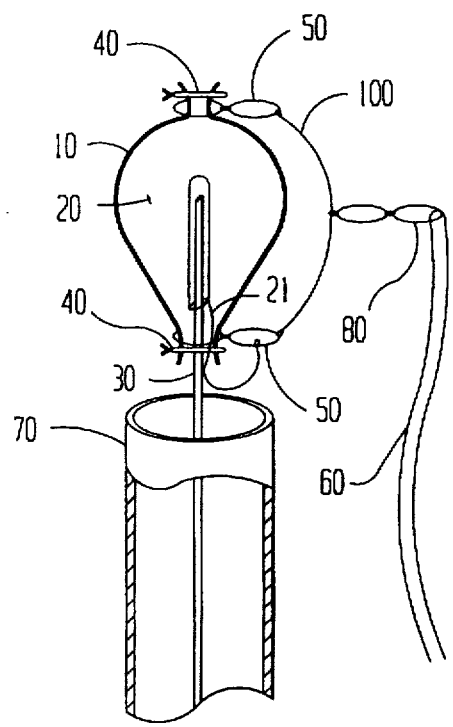
FIG. 4b is a perspective view of a non-buttoned detachable balloon for heart defect occlusion inflation. After the balloon inflation and detachment distal to the defect chamber, the balloon is pulled occluding the defect; by pulling further, the loop sheath, the floppy disk is released in the proximal to the defect chamber; subsequently the floppy disk automatically becomes straight holding the balloon from the opposite side.

FIG. 4B shows a heart defect occlusion application using a detachable balloon connected with a proximal floppy disk 130. The sac 10 is spherical or flat and a connecting loop 50 is sutured in the mouth. A floppy disk 130 is also sutured at the mouth of the balloon and it is curved during introduction (1) and straight after release.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. The method of repairing a defect in a vascular system component of a patient comprising the steps of:

introducing a sac through the skin of said patient, said sac having a sealable mouth and a volume for filling with a liquid;

placing the sac adjacent to said defect in the component;

filling the sac with a liquid, said liquid including a radiopaque component;

sealing the mouth of the sac; and tying the sac at its mouth with a holding wire, said holding wire having a first and second end, said first end being tied to the sac.

2. The method as defined in claim 1 wherein said defect is a faulty heart valve and the sac functions as an artificial valve member positioned so that the sac operates in conjunction with an existing valve annulus.

3. The method as defined in claim 1 wherein said defect is an opening, and said opening is occluded by the sac.

4. The method as defined in claim 3 further comprising retrieving the sac.

5. The method as defined in claim 3 further comprising at least temporarily tethering the sac by immobilizing said second end of said holding wire on the skin of said patient.

6. The method as defined in claim 5 further comprising holding the sac in position by using a counter occluder, and retrieving the sac if desired.

7. The method as defined in claim 5 further comprising holding the sac in position by using a sutured floppy disk, and retrieving the sac if desired.

8. The method as defined in claim 3 further comprising fixing the sac in position by attaching a counter occluder to the sac.

9. The method as defined in claim 3 further comprising fixing the sac in position by attaching a sutured floppy disk to the sac.

10. The method as defined in claim 3 wherein said opening is a septal defect, and further comprising using the sac for occluding the septal defect where there is an insufficient septal rim for other known occlusion methods.

11. The method as defined in claim 1 wherein said defect is excessive flow in an artery of the patient, and the sac is used to restrict the excessive flow in the artery.

12. The method as defined in claim 11 further comprising retrieving the sac.

13. The method as defined in claim 11 further comprising tethering the sac by immobilizing said second end of said holding wire on the skin of said patient.

14. The method as defined in claim 11 further comprising centering the sac in the artery by using a stabilizing wire attached to the mouth of the sac.

15. The method as defined in claim 11 further comprising at least temporarily tethering the sac by immobilizing said second end of said holding wire on the skin of said patient, holding the sac centered in the artery by a stabilizing wire, and retrieving the sac.

16. A device for occluding vascular system defects in a patient comprising:

a sac occluder having a sealable mouth and a volume filled with a liquid; and a holding wire, said holding wire having a first and second end, said first end being tied to the mouth of the sac;

whereby the sac occluder is capable of being held in position within the vascular system, at least temporarily, by immobilizing said second end of said wire on the skin of said patient.

17. The device of claim 16 wherein the sac occluder is flexible and conforms to a shape of the defect being occluded.

18. The device of claim 16 further comprising a counter occluder, and whereby the sac occluder may be fixed in position within the vascular system by attaching the sac occluder to said counter occluder.

19. The device of claim 16 further comprising a sutured floppy disk, and whereby the sac occluder may be fixed in position within the vascular system by attaching the sac occluder to said floppy disk.

20. The device of claim 16 whereby the sac occluder functions in operational relationship to an existing valve annulus within the vascular system to seat against said annulus during a normal operational cycle.

21. The device of claim 20 wherein the valve annulus is a heart valve annulus.

22. The device of claim 16 wherein the liquid filling the sac occluder has a radiopaque component.

* * * * *